US008423137B2

(12) United States Patent
Moulder

(10) Patent No.: US 8,423,137 B2
(45) Date of Patent: Apr. 16, 2013

(54) DEFIBRILLATOR HAVING SPECIALIZED OUTPUT WAVEFORMS

(75) Inventor: J. Christopher Moulder, Portland, OR (US)

(73) Assignee: Biotronik SE & Co. KG (DE)

( * ) Notice: Subject to any disclaimer, the term of this patent is extended or adjusted under 35 U.S.C. 154(b) by 0 days.

(21) Appl. No.: 13/340,038

(22) Filed: Dec. 29, 2011

(65) Prior Publication Data

US 2012/0179218 A1    Jul. 12, 2012

Related U.S. Application Data

(60) Provisional application No. 61/431,864, filed on Jan. 12, 2011.

(51) Int. Cl.
*A61N 1/00* (2006.01)

(52) U.S. Cl.
USPC .............................................. 607/5

(58) Field of Classification Search ........... 607/5
See application file for complete search history.

(56) References Cited

U.S. PATENT DOCUMENTS

| 6,233,483 | B1 | 5/2001 | Causey, III et al. |
| 6,647,290 | B2 * | 11/2003 | Wuthrich ............... 607/5 |
| 7,151,963 | B2 | 12/2006 | Havel et al. |
| 7,450,995 | B2 | 11/2008 | Moulder et al. |
| 2004/0068301 | A1 | 4/2004 | Waltman et al. |
| 2005/0107833 | A1 | 5/2005 | Freeman et al. |

OTHER PUBLICATIONS

Boriani, et al., "Plateau Waveform Shape Allows a Much Higher Patient Shock Energy Tolerance in AF Patients", *Journal of Cardiovascular Electrophysiology*, 18:728-734, 2007.

Fishler, M.G., "Theoretical Predictions of the Optimal Monophasic and Biphasic Defibrillation Waveshapes", *IEEE Transactions on Biomedical Engineering*, 47:59-67, 2000.

Kroll, M.W., "A Minimal Model of the Single Capacitor Biphasic Defibrillation Waveform", *Pacing and Clinical Electrophysiology* (*PACE*) 17:1782-92, 1994.

Malkin, et al., "Experimental Verification of Theoretical Predictions Concerning the Optimum Defibrillation Waveform", *IEEE Transactions on Biomedical Engineering*, 53:1492-8, 2006.

Shorofsky, et al., "Improved defibrillation efficacy with an ascending ramp waveform in humans", *Heart Rhythm*, 2:388-94, 2005.

European Search Report, Appln. No. 11193749.6-2305, May 10, 2012.

* cited by examiner

*Primary Examiner* — George Manuel
(74) *Attorney, Agent, or Firm* — Craig A. Fieschko, Esq.; DeWitt Ross & Stevens S.C.

(57) ABSTRACT

An output stage for use in a therapeutic defibrillator enables practical use of specialized output waveforms optimized for cardiac defibrillation. A pulse-width modulated (PWM) switching amplifier, connected to a high voltage source capacitor and to one or more output bridges corresponding to different electrode placements, is adapted to operate with high efficiency, demonstrated at about 80%. The amplifier is capable of delivering a defibrillating electric shock to a heart in the form of a time-varying output voltage waveform of arbitrary shape. Efficiency improvement is accomplished through the use of a high voltage reservoir capacitor network configured to minimize a voltage differential between the high voltage reservoir and the output voltage. The switching amplifier features both step-up and step-down amplifier capability. A PWM control unit is positioned within the circuit so as to reduce complexity by eliminating a need for additional isolation circuitry.

20 Claims, 6 Drawing Sheets

DEFIBRILLATOR HAVING SPECIALIZED OUTPUT WAVEFORMS

CROSS-REFERENCE TO RELATED APPLICATIONS

This patent application claims the benefit of U.S. Provisional Patent Application No. 61/431,864, filed on Jan. 12, 2011, which is hereby incorporated by reference in its entirety.

FIELD OF THE INVENTION

The invention generally relates to devices and methods for generating outputs to be delivered to a heart during defibrillation, and more specifically relates to devices and methods for energy-efficient generation of specialized/customized defibrillation waveforms.

BACKGROUND OF THE INVENTION

Cardiac fibrillation is a potentially life-threatening emergency medical condition in which the heart muscle quivers instead of contracting in a coordinated fashion. An implantable cardioverter defibrillator (ICD) is a medical device that is implanted in a patient for the purpose of automatically detecting and arresting fibrillation. The ICD restores a normal heart rhythm without requiring immediate medical intervention using an external defibrillator (e.g., electric shock "paddles"). When an ICD detects atrial or ventricular fibrillation, coordinated muscular contractions are restored by internal delivery of a therapeutic electric shock to the heart. ICD hardware includes electronics contained in a biocompatible, hermetically-sealed housing that is implanted subcutaneously in the patient's chest; and electrodes, connected to the device by leads that extend into the heart, for sensing electrical signals and for applying electric current to the heart tissue. The ICD is configured such that one electrode is placed in either the atrium or the ventricle, and the ICD housing is electrically grounded. In the same manner that an external defibrillator effects a therapeutic shock, a battery within the ICD housing supplies power to charge a capacitor, which is then suddenly discharged across the heart. Ventricular defibrillation typically involves application of higher voltages, above about 240 V, associated with an energy level of about 40 J. Atrial defibrillation, however, typically involves application of lower voltages, having a maximum value in the range of about 200-240 V, and an associated energy in the range of about 4-12 J. Lower energy is required because of the reduced mass of cardiac tissue in the atrium, compared with that in the ventricle.

A conventional ICD applies a truncated, decreasing exponential voltage waveform that terminates fibrillation at a defibrillation threshold level (DFT), or energy requirement, of about 20-30 Joules. It has been shown by R. A. Malkin, et al., *IEEE Transactions on Biomedical Engineering*, 53:1492-8, 2006, that the decreasing truncated exponential waveform is not the most efficient for defibrillation. Studies such as those presented by S. R. Shorofsky, et al., *Heart Rhythm*, 2:388-94, 2005, have shown that an increasing exponential waveform shape is the most energy efficient at a given DFT. For example, M. W. Kroll, *Pacing and Clinical Electrophysiology (PACE)* 17:1782-92, 1994, and M. G. Fishler, *IEEE Transactions on Biomedical Engineering*, 47:59-67, 2000, disclose the use of specialized waveforms, instead of the usual decreasing exponential waveform, that are capable of reducing the DFT by 20% or more, resulting in a longer battery life, increased efficacy, or reduced device size. It has also been shown by G. Boriani, et al., *Journal of Cardiovascular Electrophysiology*, 18:728-734, 2007, that a square waveform produces the least amount of pain for the patient. Pain reduction is particularly important in cases of atrial fibrillation, in which the patient is likely to be conscious while therapeutic shocks are administered.

Although the most desirable waveform shapes are known, the ability to make use of the known optimum shapes is not commercially available in ICD products due to power constraints. For example, U.S. Pat. No. 7,450,995, to the same inventor as the present patent application, discloses the use of a specialized, rising exponential waveform, which has been shown to outperform the conventional truncated, decreasing exponential waveform. However, the '995 patent fails to present a practical implementation that has a high enough efficiency to benefit from use of the specialized waveform. Fischler, *IEEE Transactions on Biomedical Engineering*, January, 2000, demonstrates that in order to realize the benefit of using an increasing exponential waveform, the efficiency of the waveform generation circuitry must exceed 66%. If the energy needed to create a specialized waveform is greater than the amount by which use of that specialized waveform decreases the DFT, then no energy savings are realized. For example, if the output stage is 50% efficient, but it only decreases the DFT by 20%, then 30% of the energy is wasted. Analysis of circuitry described in the '995 patent has demonstrated that, because it is resistor-capacitor based, its efficiency is approximately 50%, which therefore is not implementable in an implantable device. U.S. Pat. No. 7,151,963 to Havel, et al. teaches an implementation that may be capable of achieving a significantly higher efficiency. However, it appears that the use of isolated switching circuitry renders Havel's implementation too large for practical use in an implantable device. What is needed, therefore, is an implementation having switching circuitry that offers a high enough efficiency to accommodate practical use of the more desirable rising exponential waveform.

SUMMARY OF THE INVENTION

An output stage for use in a therapeutic defibrillator, an exemplary version of which is described below, provides a high level of efficiency that enables practical use of specialized output waveforms optimized for cardiac defibrillation. The output stage features a high-efficiency output amplifier circuit that is capable of delivering to a heart a defibrillating electric shock in the form of a time-varying output voltage waveform of arbitrary shape. The shape of the waveform, specified as a predetermined input to the circuit, may be programmable. In this scenario, the heart constitutes an electrical load connected through one or more output bridges associated with different electrode placements. The output amplifier circuit includes a high voltage source capacitor for storing a therapeutic amount of electrical energy for rapid discharge across the load. A pulse-width modulated (PWM) switching amplifier, connected to the high voltage source capacitor and to the output bridges, is adapted to operate with at least 70% efficiency. This is accomplished through the use of a high voltage reservoir capacitor network adapted to minimize a voltage differential between the high voltage reservoir and the output voltage. The switching amplifier disclosed herein has both step-up and step-down amplifier capability. The PWM is positioned within the circuit so as to reduce its complexity by eliminating a need for additional isolation circuitry.

DETAILED DESCRIPTION OF EXEMPLARY VERSIONS OF THE INVENTION

Figure 1:
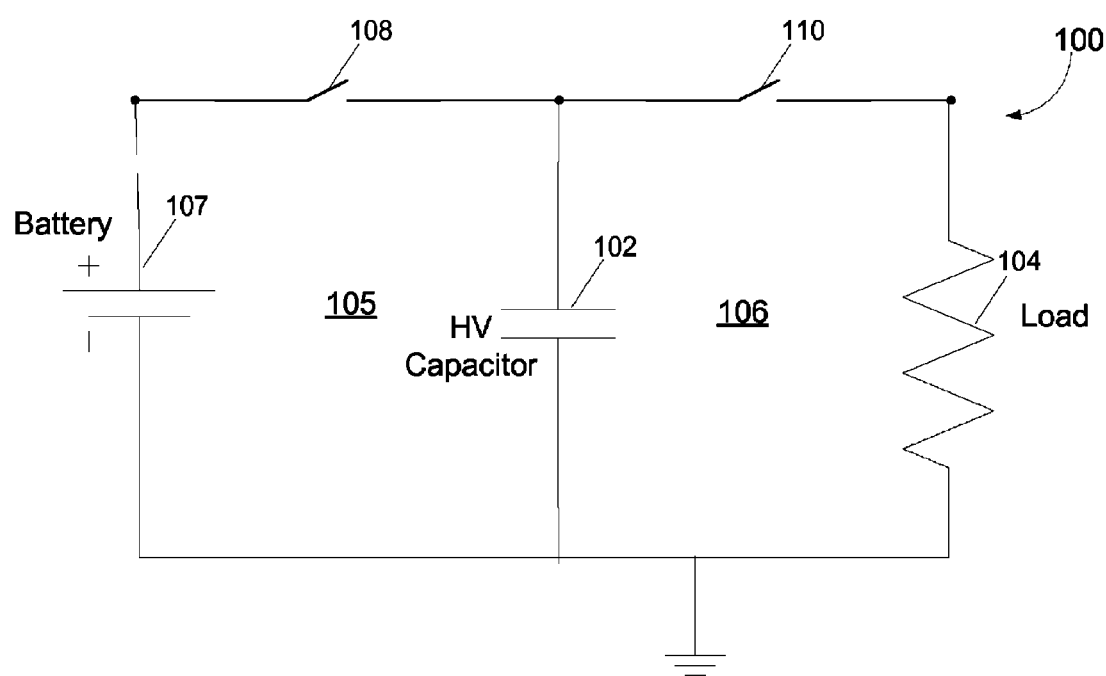
FIG. 1 is a schematic diagram of a simplified circuit model representing charging and output stages comprising the therapeutic shock unit of a defibrillator.

Versions of the present invention will be readily understood from the following detailed description in conjunction with the accompanying drawings, wherein like reference numerals designate like structural elements. The drawings illustrate exemplary versions of the invention, which is not intended to be limited to the versions shown in the drawings.

FIG. 1 shows a shocking circuit 100 for charging a high voltage (HV) capacitor 102 and then discharging capacitor 102 across a generic output load 104. Shocking circuit 100 may be understood as a simplified model for a portion of an ICD that delivers a therapeutic shock to a heart. Shocking circuit 100 includes a charging stage 105 and a discharging, or output, stage 106. In the charging stage, the power source in circuit 100—battery 107—supplies power to charge a source HV capacitor 102 when charging switch 108 is closed. After HV capacitor 102 is fully charged, charging switch 108 is opened. In the output stage, discharging switch 110 is closed in order to apply the electric potential stored in HV capacitor 102 across output load 104. In the case of an ICD application, battery 107 and HV capacitor 102 are located within the ICD housing, and output load 104 represents the heart.

Figure 2:
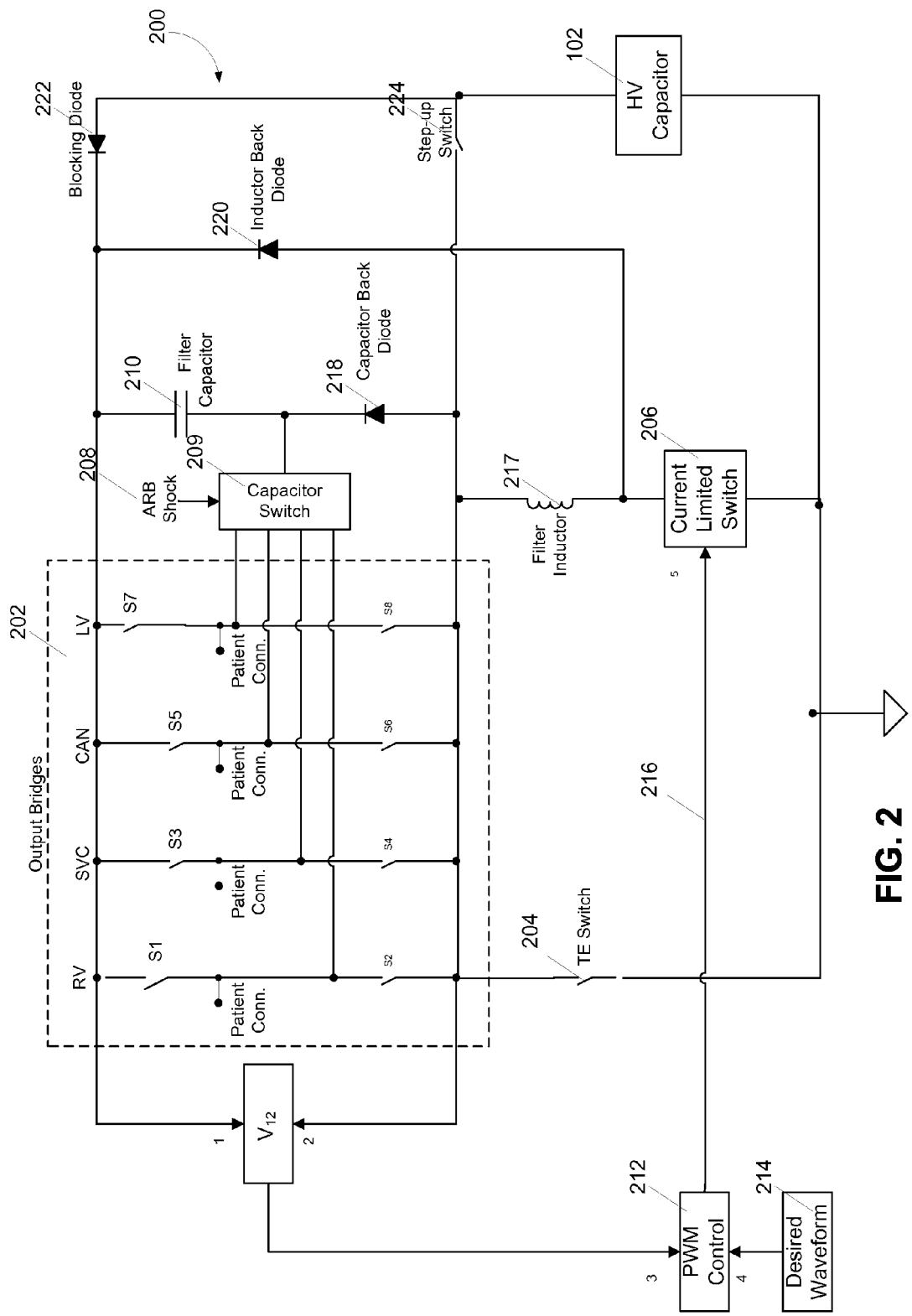
FIG. 2 is a schematic diagram of an exemplary preferred version of an output stage in which a high efficiency switching amplifier circuit generates an arbitrary, specialized, defibrillating waveform.

FIG. 2 shows a preferred version of a high-efficiency output stage 106 for implementing a method of generating arbitrary voltage waveforms, in the form of an output amplifier circuit 200. Output amplifier circuit 200 may be used in any defibrillator, but its increased efficiency and reduced complexity features make it particularly well suited to an ICD application. When properly implemented, amplifier circuit 200 becomes capable of operating with at least 70% efficiency. The ability to generate output waveforms of arbitrary shape with such high efficiency enables the practical use of novel, specialized waveforms, including waveforms that cause lower pain. Referring to FIG. 2, HV capacitor 102 is shown connected to a bank of output bridges 202 for directing high voltage waveforms to various patient electrodes, such as left ventricular (LV), right ventricular (RV), superior vena cava (SVC), and the ICD housing (CAN). LV outputs may be placed in the patient's coronary sinus or pulmonary artery so as to deliver treatment via the least painful shock vector. The switches in output bridges 202 may be made up of electronic components that include insulated gate bipolar transistors (IGBTs) and silicon controlled rectifiers (SCRs). If all of the switches within output bridges 202 are implemented using SCRs, step-up isolation devices may not be necessary to generate the desired output waveforms. Removal of the isolation circuitry significantly reduces the size and the complexity of amplifier circuit 200.

Amplifier circuit 200 may be categorized as a modified "class D amplifier" in which amplification provides an output waveform that has a higher voltage than source HV capacitor 102. Class D switching amplifiers are generally known to those skilled in the art as PWM amplifiers having circuit components that are operated as high-frequency binary switches. Rapid switching between binary states produces a square wave signal that may be used to reproduce and amplify a low-frequency sinusoidal input signal. One advantage of class D amplifiers is that, because the amplification is typically accomplished by power MOSFET switches which are either fully on, or fully off, they are highly efficient in delivering substantially all (i.e., well over 90%) of the supplied power to the load with no measurable heat dissipation. Class D switching amplifiers therefore are suitable for use in applications such as audio devices or mobile phones for which preservation of battery lifetime is a high priority.

Amplifier circuit 200 may be used to generate either a standard truncated exponential waveform, or a specialized waveform. During generation of a standard truncated exponential waveform, a truncated exponential (TE) switch 204 is closed. TE switch 204 may take the form of an IGBT or a field effect transistor (FET). During generation of arbitrary waveforms, TE switch 204 remains open, and instead, a current limited switch 206 is used to close amplifier circuit 200. An arbitrary shock waveform 208 may be applied to a capacitor switch 209 just prior to shock delivery, in order to multiplex a single filter capacitor 210 into the circuit portion formed by at least two half bridges. Capacitor switch 209 automatically connects filter capacitor 210 to whichever half bridge is currently active, thus providing simplified control. A voltage $V_{12}$ across output bridges 202, is attenuated by a pulse width modulator (PWM) control unit 212, and compared with a desired waveform 214. An output signal 216 from PWM control unit 212 is then a pulse-width modulated signal used to switch on and off current-limited switch 206. The base frequency of pulse width modulator in PWM control unit 212 is preferably in the range of about 100 kHz-1 MHz. When current-limited switch 206 is closed, current flows from HV capacitor 102 through output bridges 202 and charges filter capacitor 210 and a filter inductor 217. Placing filter inductor 217 and PWM control unit 212 on the low side of amplifier circuit 200 simplifies switching because a ground reference switching circuit may be used to eliminate the need for isolation.

Switch 206 automatically closes if too much current is drawn, for example, at the beginning of shock delivery when a large voltage gradient exists between HV capacitor 102 and the load, or output voltage on output bridges 202. When switch 206 closes (either because the current limit has been exceeded, or in response to output signal 216), the electric potential stored in filter capacitor 210 is discharged through a capacitor back diode 218 and applied to the patient. At the same time, energy stored in filter inductor 217 is released through an inductor back diode 220, and is also applied to the patient. The function of filter components 210 and 217 is to provide low-pass filtering of the class D amplifier, i.e., to filter out high-frequency switching components introduced by PWM control unit 212, in order to smooth the output signal 216. Alternatively, filter components 210 and 217 can round the output waveform if the PWM circuit is not used. Meanwhile, a blocking diode 222 prevents current from flowing back into HV capacitor 102.

Figure 3A:
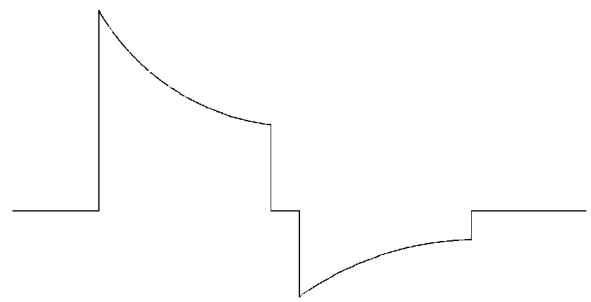
FIG. 3A is a plot of a prior art biphasic truncated exponential defibrillation waveform.
Figure 3B:
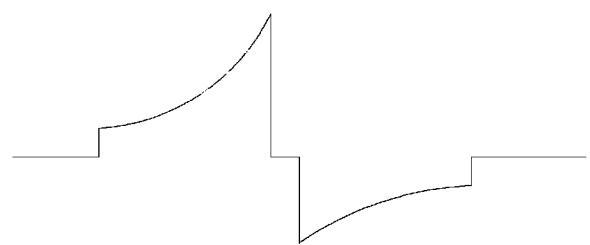
FIG. 3B is a plot of a biphasic ascending exponential waveform, predicted to be the most efficient for use in defibrillation.
Figure 3C:
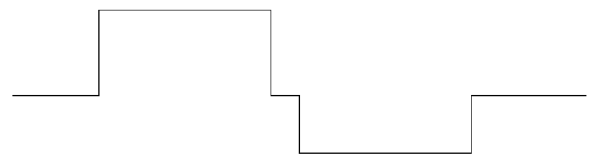
FIG. 3C is a plot of a minimum amplitude biphasic square defibrillation waveform.

Operation of the amplifier circuit 200 as a step-down amplifier continues until the potential on the HV capacitor 102 is reduced to a level close to that of the desired output waveform, at which point step-down operation of the amplifier is no longer possible. If it is desired to continue output of the shock waveform at a voltage higher than that of HV capacitor 102, a step-up switch 224 is closed. Step-up switch 224 allows current to flow in one direction only (toward the ground). Thus, when current-limited switch 206 and step-up switch 224 are both closed, step-up operation of the amplifier circuit 200 occurs such that current flows from HV capacitor 102 through step-up switch 224 and charges filter inductor 217. When current-limited switch 206 is opened, filter inductor 217 discharges through inductor back diode 226, filter capacitor 210, and the patient. Operation of amplifier circuit 200 as a step-up amplifier is less efficient than its normal operation as a step-down amplifier. Output bridges 202 are generally capable of generating a biphasic defibrillating waveform from a monophasic source. FIGS. 3A-3C show examples of biphasic specialized waveforms, in which there are both positive and a negative polarity signal portions, whereas a monophasic source provides either a positive or a negative signal. FIG. 3A illustrates a standard, state-of-the-art truncated exponentially decreasing waveform. FIGS. 3B and 3C illustrate examples of the specialized waveforms that have been shown to be most desirable, either, in the case of FIG. 3B, as the most efficient waveform for delivering energy (an increasing exponential) or, in the case of FIG. 3C, as the waveform that is most likely to minimize pain (a square wave having a low peak amplitude). The waveforms shown in FIGS. 3A-3C offer three choices that may be selected by a programmer in setting up an ICD either before implantation, or by using a remote programming device after implantation.

Figure 4:
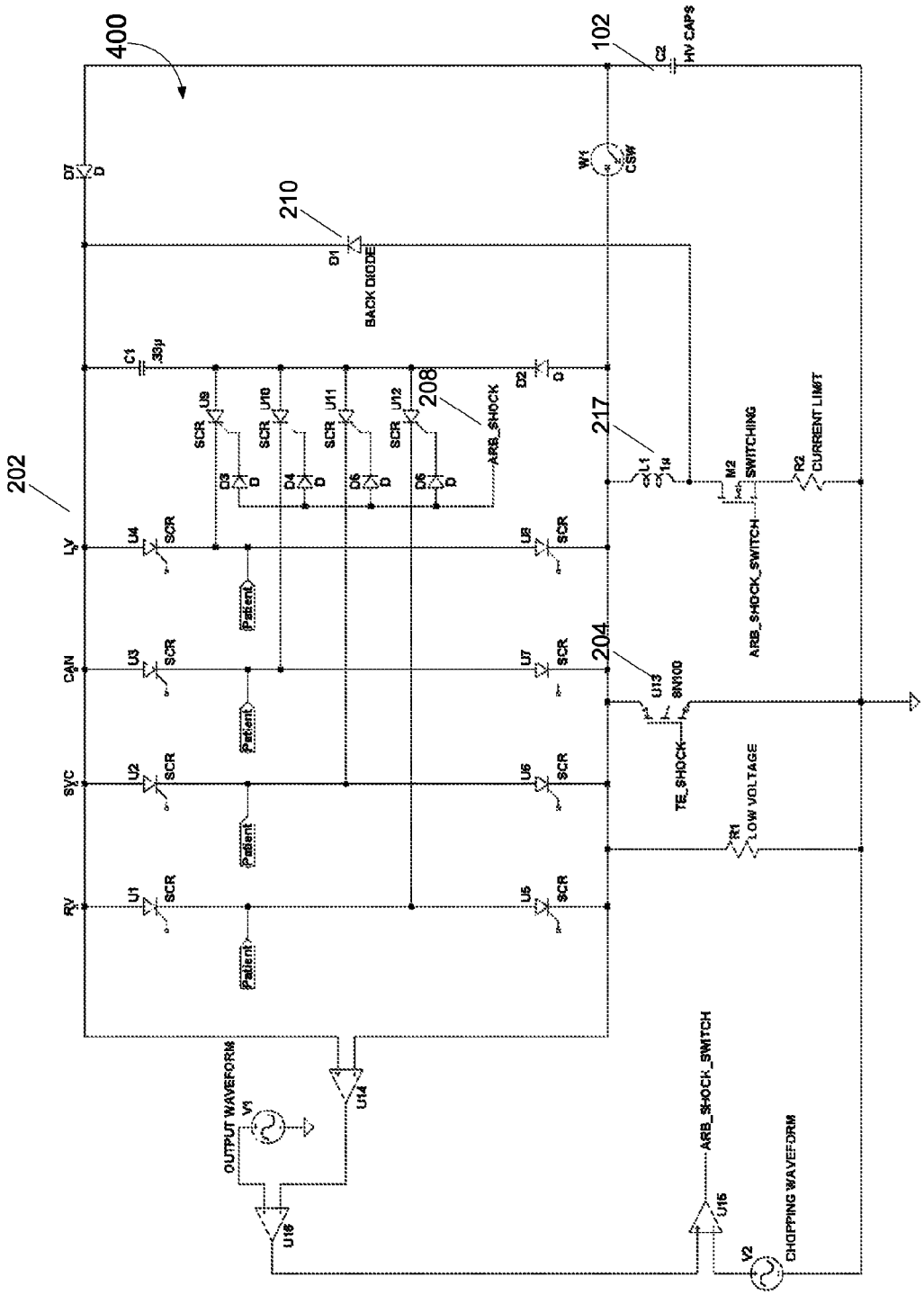
FIG. 4 is a schematic diagram of a specific exemplary implementation of the modified class D amplifier circuit shown in FIG. 2.

In general, the efficiency of amplifier circuit 200 may be modified by selecting different values for the inductors, the capacitors, and the PWM frequency. Referring to FIG. 4, circuit 400 presents a preferred implementation of amplifier circuit 200, in which certain electronic components that perform the functions of the various capacitors, inductors, and switches are specified so as to produce an overall efficiency of 80%. The speed at which the circuit can adapt and rapidly increase or decrease output voltages is dependent upon the filter components, 210 and 217 i.e., the filter capacitor and filter inductor values. For example, filter capacitor 210 is specified as having a value within the range of about 0.33 µf-2 µf, and filter inductor 217 preferably has a value within the range of about 1 µH-10 µH.

Figure 5:
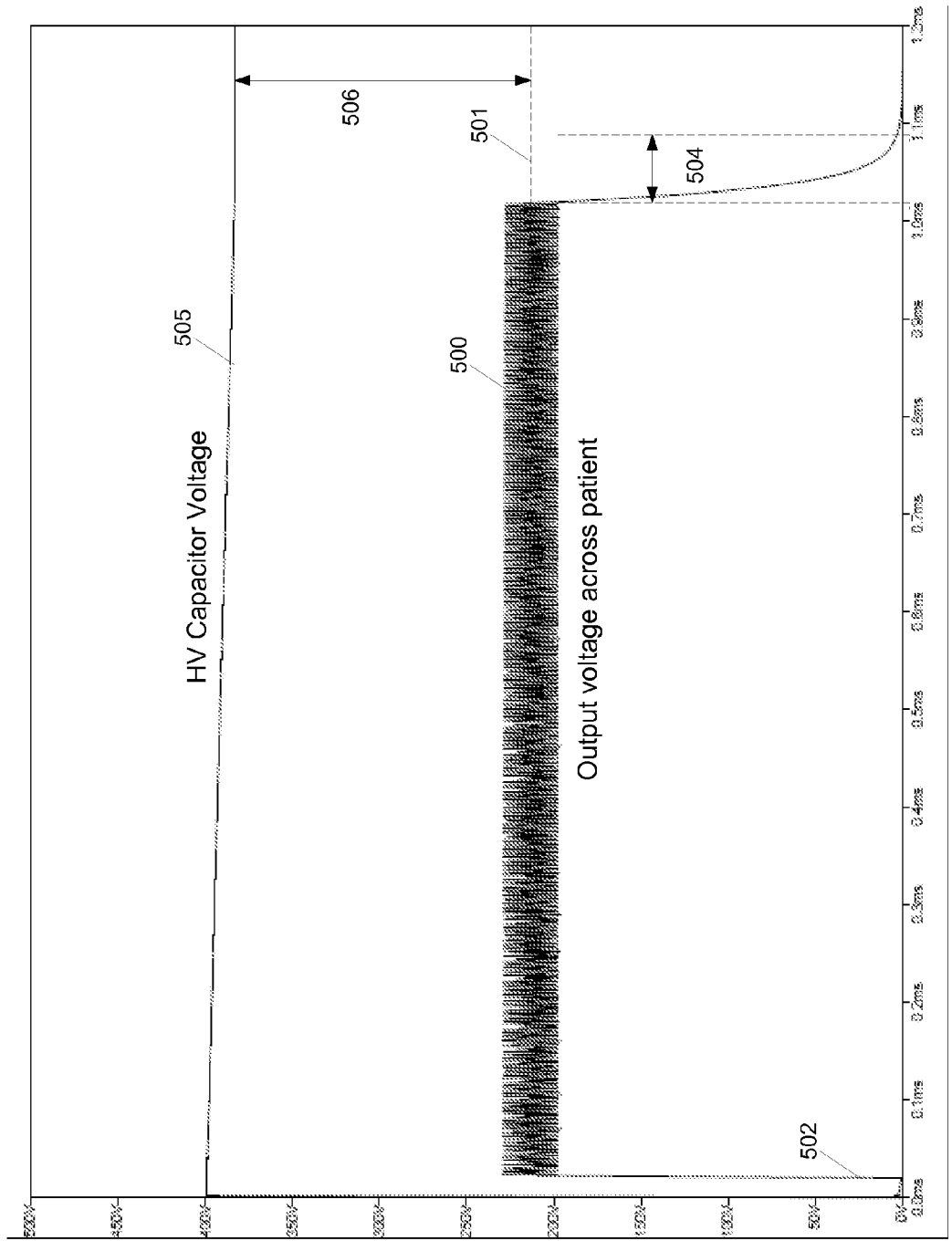
FIG. 5 is a plot, generated by a circuit simulation program, of an output voltage signal produced by the circuit of FIG. 4.

An exemplary voltage output waveform 500 characterizing circuit 400 is shown in FIG. 5, in which a fluctuating output voltage is shown as a function of time, having an average output voltage 501. Voltage output waveform 400 may obtained by running a circuit simulation of circuit 400 using the positive polarity phase of the square waveform shown in FIG. 3C. In the example output shown in FIG. 5, a rise time 502 characterizes an abrupt initiation of a 200 V defibrillating shock applied to the patient for a duration of only 1 ms, and a fall time 504 characterizes a [relatively] more gradual drop in the shock voltage, having a duration of only 0.1 ms. In addition, in this example, HV capacitor 102 is charged up to a HV capacitor voltage 505 of 400 V. The filter components 210 and 217 determine how much ripple is present in the output waveform 500. As the values of these filter components are made larger, the ripple decreases, but the rise time 502 and fall time 504 of the waveform tend to increase. In addition, an interphase delay time also increases, proportional to fall time 504, based on the values of filter components 210 and 217.

Figure 6:
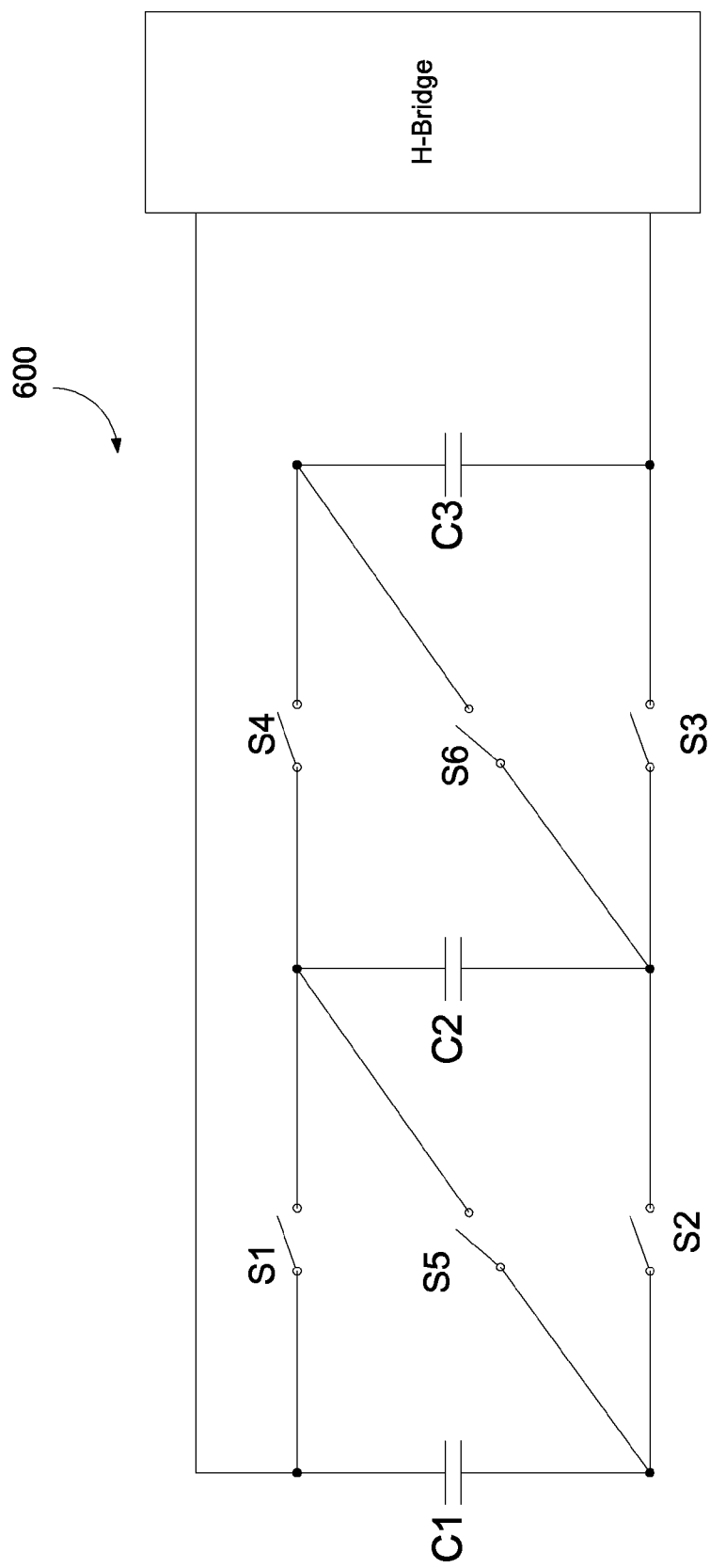
FIG. 6 is a schematic diagram of a prior art high voltage reservoir capacitor network that may be used in place of the single high voltage capacitor shown in FIG. 2, in order to match the capacitor voltage to the output voltage.

Efficiency of circuit 400 is maximized when the voltage difference, or gradient, 506 between HV capacitor voltage 505 on HV capacitor 102 and the average output voltage 501 is lowest, because minimizing this voltage differential minimizes power dissipation across the switching circuit. To maintain gradient 506 at a minimum value, several HV capacitors C1, C2, and C3 may be arranged as shown in FIG. 6 so as to adjust the resultant HV capacitor voltage 505 in accordance with variations in the average output voltage 501.

The capacitor network 600 has been used by others (e.g., U.S. Pat. No. 6,233,483) for other reasons, for example, to minimize a defibrillation threshold, but not for the present purpose of minimizing gradient 506. Other circuits may be used in place of the one shown in FIG. 6 to achieve the desired minimum gradient 506. Referring now to the exemplary version shown in FIG. 6, HV capacitor 102 may be replaced by a prior art capacitor network 600 that may be adapted to achieve a high overall efficiency of the output stage circuit 500. To accomplish this, capacitors C1, C2, and C3 each may be charged to a desired voltage by opening or closing switches S1-S6 to configure the capacitors either in series or in parallel, whichever is most beneficial. Switches S1-S6 may be FETs, SCRs, or diodes, depending on the desired operation. For example, the capacitors may all be charged to the same initial voltage, V. If the desired average output voltage 501 for output waveform 500 is less than V, the capacitors may remain in a parallel configuration by maintaining switches S5 and S6 open while closing switches S1-S4. However, if the resultant HV capacitor voltage 505 decreases to a level that inhibits operation of the amplifier circuit 200 as a step-down amplifier, the capacitors C1-C3 may be re-configured in series, by opening switches S1-S4 and closing S5 and S6, to increase HV capacitor voltage 505 High-efficiency operation then continues until HV capacitor voltage 505 again decreases to average output voltage 501, at which time either the amplitude of voltage output waveform 500 may be lowered, or the switching circuit 400 may be converted to a step-up amplifier for use in raising HV capacitor voltage 505. Thus, adaptive implementation of capacitor network 600 within amplifier circuit 200 allows more energy to be transferred from HV capacitor 102 to the patient than in existing ICDs.

Although certain versions of the invention have been illustrated and described herein, it will be appreciated by those of ordinary skill in the art that a wide variety of alternative or equivalent versions or implementations, intended to achieve the same purposes, may be substituted for the versions illustrated and described without departing from the scope of the present invention. Those with skill in the art will readily appreciate that versions in accordance with the present invention may be implemented in a very wide variety of ways. This application is intended to cover any adaptations or variations of the versions discussed herein.

The terms and expressions which have been employed in the foregoing specification are used therein as terms of description and not of limitation, and there is no intention, in the use of such terms and expressions, to exclude equivalents of the features shown and described or portions thereof, it being recognized that the scope of the invention is defined and limited only by the claims that follow.

It will be apparent to those skilled in the art that numerous modifications and variations of the described examples and versions are possible in light of the above teaching. The disclosed examples and versions are presented for purposes of illustration only. Therefore, it is the intent to cover all such modifications and alternate versions as may come within the true scope of this invention.

The invention claimed is:

1. A method of generating defibrillator output voltage waveforms using a defibrillator having a defribrillator output circuit,
   a. the output circuit including a pulse width modulator (PWM) switching amplifier having:
      (1) a filter capacitor;
      (2) a filter inductor; and
      (3) a high voltage capacitor having a high voltage capacitor voltage;
   b. the method including the steps of:

(1) generating, via the switching amplifier, a low frequency output voltage waveform having a predetermined waveform shape and an output voltage; and
(2) operating the switching amplifier as a step-down amplifier or a step-up amplifier.

2. The method of claim 1 further including the step of minimizing a voltage differential between the output voltage and the high voltage capacitor voltage, whereby at least 70% efficient operation of the switching amplifier is achieved.

3. The method of claim 2 wherein:
a. the output circuit further includes a capacitor network; and
b. the step of minimizing the voltage differential includes adjusting the capacitor network in response to changes in the voltage differential.

4. The method of claim 3 wherein:
a. the capacitor network includes network capacitors and capacitor network switches; and
b. the step of adjusting the capacitor network includes the step of opening or closing each of the capacitor network switches to configure the network capacitors in series or in parallel.

5. The method of claim 1 wherein:
a. the defibrillator is an implantable cardioverter defibrillator (ICD);
b. the output circuit further includes a bank of output bridges configured to direct the output voltage waveforms to patient electrodes; and
c. the bank of output bridges includes only silicon controlled rectifier switches such that isolation circuitry is not required to generate output voltage waveforms.

6. The method of claim 5 wherein:
a. the output circuit further includes a truncated exponential switch connected to the bank of output bridges; and
b. the method further includes the step of generating a truncated exponential waveform by closing the truncated exponential switch.

7. The method of claim 1 further including the step of generating arbitrary waveforms.

8. The method of claim 7 wherein:
a. the output circuit further includes:
   (1) a bank of output bridges;
   (2) a truncated exponential switch connected to the bank of output bridges; and
   (3) a current limited switch; and
b. the method of generating arbitrary waveforms includes the steps of:
   (1) opening the truncated exponential switch; and
   (2) using the current limited switch to close the switching amplifier.

9. The method of claim 8 wherein the filter capacitor and the filter inductor are configured to provide low-pass filtering of the switching amplifier.

10. The method of claim 1 wherein:
a. the filter capacitor has a value between at least substantially 0.33 microfarads and at least substantially 2 microfarads; and
b. the filter inductor has a value between at least substantially 1 microhenry and at least substantially 10 microhenries.

11. The method of claim 1 wherein:
a. the output circuit:
   (1) includes a single filter capacitor multiplexed to a plurality of different loads; and
   (2) further includes a capacitor network; and
b. the method further includes the step of minimizing a voltage differential between the output voltage and the high voltage capacitor voltage.

12. The method of claim 11 wherein the capacitor network is reconfigurable between:
a. a configuration wherein the capacitor network steps down the voltage differential between the high voltage reservoir capacitor and the output bridges; and
b. a configuration wherein the capacitor network steps up the voltage differential between the high voltage reservoir capacitor and the output bridges.

13. A defibrillator having a defibrillator output circuit for generating output voltage waveforms,
a. the output circuit including a pulse width modulator (PWM) switching amplifier having:
   (1) a filter capacitor;
   (2) a filter inductor; and
   (3) a high voltage source capacitor;
b. wherein the switching amplifier is configured to:
   (1) generate a low frequency output voltage waveform having a predetermined waveform shape and an output voltage; and
   (2) operate as a step-down amplifier or a step-up amplifier.

14. The defibrillator of claim 13 wherein the switching amplifier is further configured to minimize a voltage differential between the output voltage and the high voltage source capacitor such that at least 70% efficient operation of the switching amplifier is achieved.

15. The defibrillator of claim 14 wherein:
a. the output circuit further includes a capacitor network having network capacitors and capacitor network switches; and
b. the capacitor network is configured to minimize the voltage differential by opening or closing each of the capacitor network switches to adjust the connections between the network capacitors.

16. The defibrillator of claim 13 wherein:
a. the output circuit further includes:
   (1) a bank of output bridges configured to direct the output voltage waveforms to patient electrodes; and
   (2) a truncated exponential switch connected to the bank of output bridges; and
b. the output circuit is configured to generate a truncated exponential waveform when the truncated exponential switch is closed.

17. The defibrillator of claim 13 wherein:
a. the output circuit further includes:
   (1) a bank of output bridges;
   (2) a truncated exponential switch connected to the bank of output bridges; and
   (3) a current limited switch; and
b. the output circuit is configured to generate arbitrary waveforms when:
   (1) the truncated exponential switch is open; and
   (2) the switching amplifier is closed by the current limited switch.

18. A defibrillator having defibrillator output circuit including:
a. two or more output bridges;
b. a single filter capacitor multiplexed to each of the output bridges;
c. a high voltage capacitor; and
d. a reconfigurable capacitor network configured to minimize a voltage differential between the high voltage capacitor and the output bridges, wherein the capacitor network is reconfigurable between:
   (1) a configuration wherein the capacitor network steps down the voltage differential between the high voltage capacitor and the output bridges, and
   (2) a configuration wherein the capacitor network steps up the voltage differential between the high voltage reservoir capacitor and the output bridges.

19. The defibrillator of claim 18 further including a current-limited switch and a filter inductor that are both positioned at a low voltage side of the output circuit.

20. The defibrillator of claim 18 wherein the output circuit operates at an efficiency greater than 70%.

* * * * *